United States Patent
Kim

(10) Patent No.: US 10,533,019 B2
(45) Date of Patent: Jan. 14, 2020

(54) METHOD FOR MANUFACTURING 7ALPHA-ALKOXYOXACEPHEM INTERMEDIATE COMPOUND

(71) Applicants: DONGDO CO., LTD., Seoul (KR); Tianjin GreenPine Pharma Co., Ltd., Tianjin (CN)

(72) Inventor: Dong Chan Kim, Seoul (KR)

(73) Assignees: DONGDO CO., LTD., Seoul (KR); TIANJIN GREENPINE PHARMA CO., LTD., Tianjin (CN)

( * ) Notice: Subject to any disclaimer, the term of this patent is extended or adjusted under 35 U.S.C. 154(b) by 0 days.

(21) Appl. No.: 16/108,234

(22) Filed: Aug. 22, 2018

(65) Prior Publication Data

US 2019/0077812 A1    Mar. 14, 2019

(30) Foreign Application Priority Data

Sep. 13, 2017 (KR) ........................ 10-2017-0117032

(51) Int. Cl.
| | | |
|---|---|---|
| C07D 505/06 | (2006.01) | |
| C07D 505/20 | (2006.01) | |
| C07D 505/10 | (2006.01) | |
| C07D 498/04 | (2006.01) | |

(52) U.S. Cl.
CPC ......... C07D 505/06 (2013.01); C07D 498/04 (2013.01); C07D 505/10 (2013.01); C07D 505/20 (2013.01)

(58) Field of Classification Search
CPC ... C07D 505/00; C07D 505/06; C07D 498/04
See application file for complete search history.

(56) References Cited

U.S. PATENT DOCUMENTS

| | | | | |
|---|---|---|---|---|
| 4,232,151 A | * | 11/1980 | Nagata | C07D 205/085 540/301 |
| 4,323,567 A | * | 4/1982 | Narisada | A61K 31/535 514/210.08 |
| 4,532,233 A | * | 7/1985 | Tsuji | C07D 505/00 514/63 |

FOREIGN PATENT DOCUMENTS

| | | | | |
|---|---|---|---|---|
| CN | 103183686 A | * | 7/2013 | |
| GB | 1547351 A | * | 6/1979 | ........... A61K 31/535 |
| KR | 10-0899325 | | 5/2009 | |
| KR | 101292750 B1 | * | 8/2013 | |
| KR | 20130090472 A | * | 8/2013 | |
| WO | WO-2006006290 A1 | * | 1/2006 | ........... C07D 505/00 |
| WO | WO-2007105253 A2 | * | 9/2007 | ........... C07D 501/02 |
| WO | WO-2014017797 A1 | * | 1/2014 | ......... A61K 31/5365 |

OTHER PUBLICATIONS

Y. Nishitani et al., The Journal of Antibiotics (1988) (Year: 1988).*
M. Yoshioka et al., 21 Tetrahedron Letters (1980) (Year: 1980).*
M. Narisada et al., Journal of Medicinal Chemistry (1987) (Year: 1987).*
S. Uyeo et al., Journal of Medicinal Chemistry (1979) (Year: 1979).*
Y.H. He et al., Chinese Chemical Letters (2012) (Year: 2012).*
English-Language Machine Translation of KR KR-101292750 (2013) (Year: 2013).*
M. Narisada et al., Journal of Medicinal Chemistry (1979) (Year: 1979).*

* cited by examiner

*Primary Examiner* — Alexander R Pagano
(74) *Attorney, Agent, or Firm* — Norton Rose Fulbright US LLP

(57) ABSTRACT

The present disclosure provides a method for preparing a 7α-alkoxyoxacephem intermediate compound, the method comprising a process (S1) including: reacting a compound represented by a following chemical formula 1 with a halogen compound in an organic solvent to form a reaction product such that unreacted halogen compound remains; and adding metal alkoxide and reducing agent to the reaction product with the unreacted halogen compound remaining, thereby to produce a compound represented by a following chemical formula 2:

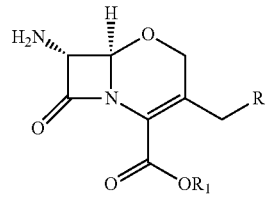

<chemical formula 1>

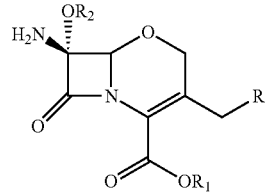

<chemical formula 2> where R is a Cl, Br, I, halogen derivative, $R_1$ is a carboxyl protecting group including diphenylmethyl, p-methoxybenzyl, p-nitrobenzyl or hydrogen (H), and $R_2$ is an alkyl group having 1 to 4 carbon atoms.

12 Claims, No Drawings

METHOD FOR MANUFACTURING 7ALPHA-ALKOXYOXACEPHEM INTERMEDIATE COMPOUND

CROSS-REFERENCE TO RELATED APPLICATION

The present application claims the benefit of Korean patent application No. 10-2017-0117032 filed on Sep. 13, 2017, the entire content of which is incorporated herein by reference for all purposes as if fully set forth herein.

BACKGROUND

Technical Field

The present disclosure relates to a method for preparing a 7α-alkoxyoxacephem intermediate compound, and more particularly to a method for preparing a 7α-alkoxyoxacephem intermediate compound, in which the manufacturing process is simple, continuous, and mass-production is easy, and yield is excellent.

Discussion of Related Art

Flomoxef acid is used as the main raw material which is pH-adjusted using sodium bicarbonate as a salt change material. Thus-pH-adjusted solution is lyophilized to prepare flomoxef sodium. Alternatively, latamoxef acid is used as the main raw material which is pH-adjusted using sodium bicarbonate as a salt change material. Thus-pH-adjusted solution is lyophilized to prepare latamoxef sodium. In this way, the flomoxef sodium or latamoxef sodium may be generated as oxacephem-based antibiotics, one of the leading antibiotics in the antibiotic market.

Important intermediate compounds that are generated during the industrial production of 1-oxacysephalosporins such as latamoxef or flomoxef with high efficiency include 7a-methoxy-1-oxacetabalphospholine derivatives. In the process for producing such an intermediate, $Cl_2$ is added to t 3-exomethylene-1-oxacetahalosporin compound as a raw material via light irradiation to perform 7α-methoxylation. However, such light irradiation generally requires expensive photoreaction equipment, and therefore is not industrially advantageous.

In addition, in this method obtain, 7α-methoxy-1-oxacysephalosporin compound from 3-exomethylene-1-oxacysephalosporin compound, the Intermediate compound is synthesized, is isolated once, and synthesized by reacting the product with chlorine in the presence of pyridine as a base. However, this method provides a lower yield.

PRIOR ART DOCUMENT

Patent Literature (Patent Document 1) KR 10-1292750 B (2013 Jul. 29)
(Patent Document 2) KR 10-2008-0111062 A (Dec. 22, 2008)

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

Thus, the present disclosure is to provide a method for preparing a 7α-alkoxyoxacephem intermediate compound, in which the manufacturing process is simple, continuous, and mass-production is easy, and yield is excellent. Further, the present disclosure is to provide 7α-alkoxyoxacephem intermediate compound as produced using the method.

In a first aspect of the present disclosure, there is provided a method for preparing a 7α-alkoxyoxacephem intermediate compound, the method comprising a process (S1) including: (a) reacting a compound represented by a following chemical formula 1 with a halogen compound in an organic solvent to form a reaction product such that unreacted halogen compound remains; and (b) adding metal alkoxide and reducing agent to the reaction product with the unreacted halogen compound remaining, thereby to produce a compound represented by a following chemical formula 2:

<chemical formula 1>

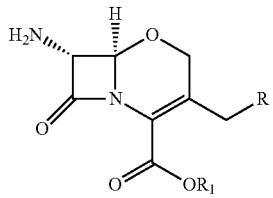

where R is a Cl, Br, I, halogen derivative, $R_1$ is a carboxyl protecting group including diphenylmethyl, p-methoxybenzyl, p-nitrobenzyl or hydrogen (H), <chemical formula 2>

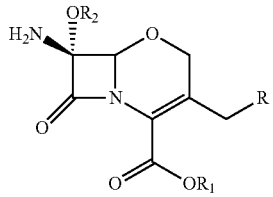

where R is a Cl, Br, I, halogen derivative, $R_1$ is a carboxyl protecting group including diphenylmethyl, p-methoxybenzyl, p-nitrobenzyl or hydrogen (H), and $R_2$ is an alkyl group having 1 to 4 carbon atoms.

In one embodiment of the first aspect, a content of the organic solvent is equal to a content of the compound expressed by the chemical formula 1 or is 100 times or less larger than the content of the compound expressed by the chemical formula 1.

In one embodiment of the first aspect, the halogen compound includes at least one selected from a group consisting of chlorine, bromine, N-iodosuccinimide, N-bromosuccinimide, N-chlorosuccinimide, N-fluorosuccinimide, tert-butyl hyperchloride, or a combination thereof.

In one embodiment of the first aspect, a content of the halogen compound is in a range of 2 to 4 mol based on a content of the compound expressed by the chemical formula 1.

In one embodiment of the first aspect, a reaction temperature in the (a) is in range of −50 to 50° C.

In one embodiment of the first aspect, the metal alkoxide includes at least one selected from a group consisting of lithium methoxide ($LiOCH_3$), lithium ethoxide, lithium tert-butoxide, sodium methoxide ($NaOCH_3$), potassium methoxide ($KOCH_3$), or magnesium methoxide ($Mg(OCH_3)_2$).

In one embodiment of the first aspect, a content of the metal alkoxide is in a range of 3 to 5 mol based on a content of the compound expressed as the chemical formula 1.

In one embodiment of the first aspect, a reaction temperature in the (b) is in a range of −70° C. to −20° C.

In one embodiment of the first aspect, the reducing agent includes at least one selected from a group consisting of sodium sulfite, sodium thiosulfate, sodium acid sulfite, dialkyl sulfide or phosphine.

In one embodiment of the first aspect, the method further comprises a process (S2) after the process (S1), wherein the process (S2) includes adding an acetamidating agent to the compound represented by the chemical formula 2, thereby to form a compound expresses by a following chemical formula 3:

<chemical formula 3>

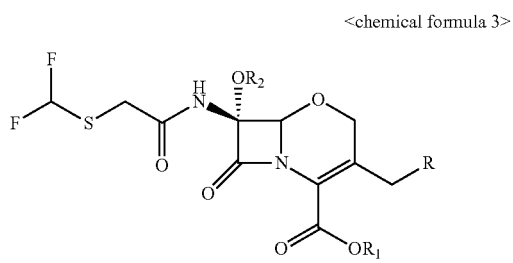

where R is a Cl, Br, I, halogen derivative, $R_1$ is a carboxyl protecting group, such as diphenylmethyl, p-methoxybenzyl, p-nitrobenzyl or hydrogen (H), and $R_2$ is an alkyl group having 1 to 4 carbon atoms.

In one embodiment of the first aspect, the acetamidating agent includes a compound expressed by a following chemical formula 4:

<chemical formula 4>

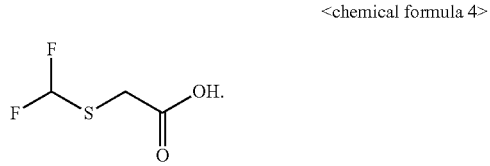

In one embodiment of the first aspect, the method further comprises a process (S3) after the process (S1), wherein the process (S3) includes adding a thiolating agent to the compound represented by the chemical formula 2, thereby to form a compound expresses by a following chemical formula 5:

<chemical formula 5>

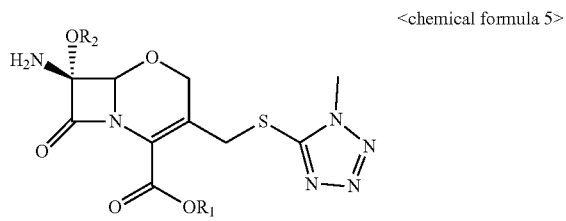

where R is a Cl, Br, I, halogen derivative, $R_1$ is a carboxyl protecting group, such as diphenylmethyl, p-methoxybenzyl, p-nitrobenzyl or hydrogen (H), and $R_2$ is an alkyl group having 1 to 4 carbon atoms.

In one embodiment of the first aspect, the thiolating agent includes a compound represented by a following chemical formula 6:

<chemical formula 6>

In a second aspect of the present disclosure, there is provided a 7α-alkoxyoxacephem intermediate compound, wherein the compound is produced by the above defined methods.

In accordance with the present disclosure, the method for preparing the 7α-alkoxyoxacephem intermediate compound is simple, continuous, and allows mass-production, and has good yield. Further, in accordance with the present disclosure, the 7α-alkoxyoxacephem intermediate compound may be produced in a simple, continuous, and mass-productive manner with a good yield thereof.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

Descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure."

The method for preparing the 7α-alkoxyoxacephem intermediate compound according to the present disclosure a include a process S1 in which a compound represented by a following chemical formula 1 reacts with a halogen compound in an organic solvent to form a reaction production and, with unreacted halogen compound remaining, metal alkoxide and reducing agents are added to the reaction product, to produce a compound represented by a following chemical formula 2:

<Chemical formula 1>

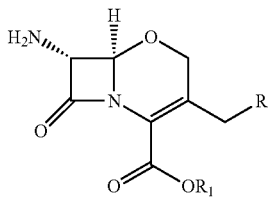

where R is a Cl, Br, I, halogen derivative, $R_1$ is a carboxyl protecting group including diphenylmethyl, p-methoxybenzyl, p-nitrobenzyl or hydrogen (H), <Chemical formula 2>

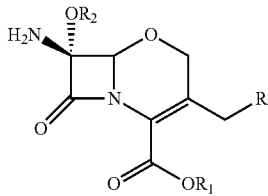

where R is a Cl, Br, I, halogen derivative, $R_1$ is a carboxyl protecting group, such as diphenylmethyl, p-methoxybenzyl, p-nitrobenzyl or hydrogen (H), and $R_2$ is an alkyl group having 1 to 4 carbon atoms.

In the process S1, the compound represented by the chemical formula 1 is reacted with the halogen compound in the organic solvent to produce the compound represented by the chemical formula 2.

As long as in the organic solvent, 7-amino-3-chloromethyl-1-oxa-3-cephem-4-carboxylic acid derivative as an example of the chemical formula 1 may easily react with the halogen compound, the organic solvent is not particularly limited. For example, the organic solvent may employ a solvent such as methylene chloride, acetone, ketones such as methyl ethyl ketone, methyl formate, esters such as ethyl acetate, ethers such as diethyl ether, tetrahydrofuran, halogenated hydrocarbons such as dichloromethane, chloroform, or nitrile such as acetonitrile. etc.

The content of such an organic solvent may be equal to the content of the reactant (i.e., the chemical formula 1), or may be 100 times or less than that of the reactant. If the content of such an organic solvent is too small, there is a risk of side reactions. If the content of the organic solvent is too high, the reaction rate may be lowered.

Further, the halogen compound may include chlorine, bromine, N-iodosuccinimide, N-bromosuccinimide, N-chlorosuccinimide, N-fluorosuccinimide, tert-butyl hyperchloride, or a combination thereof.

The content of such a halogen compound may be at least 2 mol, preferably from 2 to 4 mol, more preferably from 2 to 3 mol, most preferably from 2.5 to 3 mol, based on the content of the reactant.

In this connection, in order to prepare the product of the chemical formula 2 from the reactant, 2 mol of the content of the halogen compound may suffice. According to the present disclosure, when the halogen compound has a content exceeding the above range, the remaining unreacted halogen compound may have an effect of efficiently advancing the subsequent reaction. Therefore, the halogen compound may exceed the above range. This is particularly preferable when one-pot reaction is employed.

Further, the reaction temperature may be −50 to 50° C., preferably about −10 to 25° C. The reaction time may vary depending on the reaction temperature. In the above temperature range, the reaction time may be from about 1 to 9 hours, preferably from 1 to 2 hours.

As mentioned above, the continuous reaction may be performed in the one-port process with the excess of the content of the halogen compound.

The metal alkoxide may replace the oxide at the 7-position of the reactant. For example, the metal alkoxide may include at least one selected from a group consisting of lithium methoxide ($LiOCH_3$), lithium ethoxide, lithium tert-butoxide, sodium methoxide ($NaOCH_3$), potassium methoxide ($KOCH_3$), or magnesium methoxide ($Mg(OCH_3)_2$). The lithium methoxide may be preferably employed from the viewpoint of the reaction efficiency.

The content of such metal alkoxide may be at least 3 mol, preferably about 3 to 5 mol, more preferably about 3.5 to 4.2 mol, based on the content of the compound of chemical formula 1.

In addition, the metal alkoxide may be mixed with methanol to form a solution which in turn may be added. The reaction temperature may be generally −70° C. to −20° C., preferably −60° C. to −30° C., more preferably −50° C. to −40° C. The reaction time may be from 1 hour to 10 hours, preferably from 2 to 3 hours.

Due to the addition of the metal alkoxide, the substitution at the 7-position of the reaction occurs. Thus, it is necessary to reduce N—Cl at the 7-position with NH. For this reason, a reducing agent that realizes such reduction may be used. Examples of the reducing agent may include sodium sulfite, sodium thiosulfate, sodium acid sulfite, dialkyl sulfide (e.g., dimethyl sulfide) or phosphine (e.g., triphenylphosphine).

Such a reducing agent may be added in the form of an aqueous solution, in which, the reducing agent preferably has 1 to 10% by weight, more preferably 5 to 10% by weight, based on that of water.

Furthermore, the content of the reducing agent may be 1 to 10 mol, preferably 1 to 6 mol, relative to the content of chemical formula 1. The reaction temperature may be from 0° C. to 50° C., preferably from 5° C. to 30° C. The reaction time may be from 1 minute to 10 hours, preferably from 10 minutes to 1 hour.

Then, according to the present disclosure, after process S1, an acetamidating agent is added in process S2 to generate a compound of the following chemical formula 3:

<Chemical formula 3>

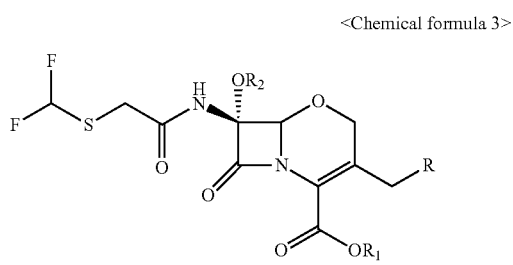

where R is a Cl, Br, I, halogen derivative, $R_1$ is a carboxyl protecting group, such as diphenylmethyl, p-methoxybenzyl, p-nitrobenzyl or hydrogen (H), and $R_2$ is an alkyl group having 1 to 4 carbon atoms.

In this connection, the acetamidating agent may include a compound expressed as a following chemical formula 4:

<Chemical formula 4>

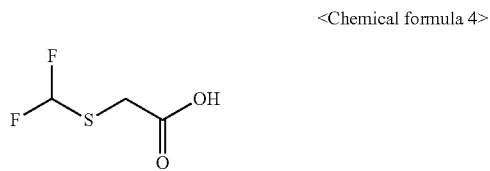

Further, according to the present disclosure, in process S3 after the process S1, a thiolating agent may be added to produce a compound of the following chemical formula 5:

<Chemical formula 5>

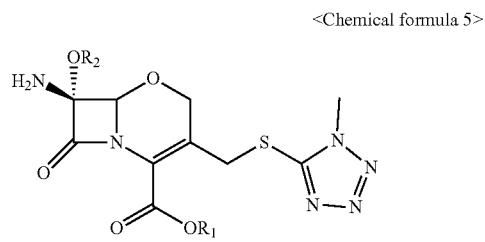

where R is a Cl, Br, I, halogen derivative, $R_1$ is a carboxyl protecting group, such as diphenylmethyl, p-methoxybenzyl, p-nitrobenzyl or hydrogen (H), and $R_2$ is an alkyl group having 1 to 4 carbon atoms.

The thiolating agent as described above may be a compound represented by the following chemical formula 6:

<Chemical formula 6>

At this point, the reaction is terminated in the corresponding process. Accordingly, the chemical formula 3 prepared by the above-described preparation method according to the present disclosure may be a 7α-alkoxyoxacephem intermediate compound used for producing flomoxef acid. Further, the chemical formula 5 prepared by the above-described preparation method according to the present disclosure may be a 7α-alkoxyoxacephem intermediate compound used for preparing latamoxef acid.

Example 1: Production of (6R, 7R)-benzhydryl-7-(difluoromethylthio)acetamido)-3-(chloromethyl)-7-methoxy-8-oxo-5-oxa-1-aza-bicyclo[4,2,0]oct-2-ene-2-carboxylate First, 450 g of methylene chloride is added into 50.0 g (0.13 mol) of 7-amino-3-chloromethyl-1-oxa-3-cephem-4-carboxylic acid diphenyl ester as a starting material and then is cooled to −20 degree C. Thereafter, 29.0 g (0.4 mol) of chlorine is injected for 60 minutes to form a first mixture. The mixture is stirred at the same temperature for 10 minutes. Then, 174.7 g (0.46 mol) of a methanol solution of 10% LiOMe (lithium methoxide) is added to the first mixture in a dropwise manner at −40 to −50 degree C. for 90 minutes to form a second mixture. Then, at the same temperature, after stirring the second mixture for 5 minutes, 6.4 g (0.11 mol) of acetic acid is added thereto. Then, 428.5 g of 10% sodium sulfite, and 400 g of purified water are added in this order to the second mixture to form a third mixture. After stirring the third mixture for 30 minutes, the methylene chloride layer is separated from the third mixture. Thereafter, the third mixture is washed using a dilute aqueous sodium bicarbonate solution. Then, 50 g of anhydrous magnesium sulfate is added to an organic layer of the third mixture, followed by stirring for 20 minutes, followed by filtration and, followed by washing with 200 g of methylene chloride. In this way, an intermediate product is obtained.

Then, 10.7 g of pyridine is added to the intermediate product which in turn, cooled to below −45° C. Subsequently, a mixed solution of 200 g of methylene chloride, 22.7 g (0.13 mol) of difluoromethylthioacetic acid, and 26.8 g of phosphorus tetrachloride as maintained at −45° C. is added to the intermediate product for 30 minutes. At this time, the temperature is kept at −25° C. Then, the intermediate product is stirred for 60 minutes at −15 degree C. Thus, the reaction is terminated. In this way, a second intermediate product is obtained. Thereafter, 150 g of purified water and 2.5 g of tetrabutylammonium bromide are added dropwise in this order to the second intermediate product which in turn, is stirred at 0 degree C. for 10 minutes. Subsequently, 100 g of methanol are added to the second intermediate product, which is stirred for 10 minutes at 0 degree C. An organic layer is separated from the intermediate product. The organic layer is concentrated at 80% or more, and, then, 100 g of ethanol is added to the organic layer which is reconcentrated. Then, 100 g of ethanol is further added to the organic layer, which in turn, is stirred at −10 DEG C. for 2 hours and then filtered. Then, the layer is washed with 50 g of ethanol and vacuum-dried at 40 DEG C. for 10 hours. Eventually, a white crystalline powder, (6R, 7R)-benzhydryl-7-(difluoromethylthio)acetamido)-3-(chloromethyl)-7-methoxy-8-oxo-5-oxa-1-aza-bicyclo[4,2,0]oct-2-ene-2-carboxylate (48.6 g, 70%) having following properties is obtained:

m.p.: 181 to 183° C.

H-NMR (CDCl$_3$) δ: 3.59 (3H, s, C7-OCH$_3$), 3.61 (2H, s, S—CH$_2$), 4.53 (2H, s, C2-H), 4.52-4.55 (2H, d, C3-CH$_2$), 5.18 (1H, s, C6-H), 6.79-7.15 (1H. t, S—CHF$_2$), 7.02 (1H, s, CHPh$_2$), 7.31-7.62 (11H, m, C$_6$H$_5$, NH)

Example 2: Producing of (6R, 7R)-benzhydryl-7-amino-7-methoxy-3-((1-methyl-1H-tetrazol-5-ylthio) methyl)-8-oxo-5-oxa-1-aza-bicyclo[4.2.0]oct-2-ene-2-carboxylate First, 450 g of methylene chloride is added into 50.0 g (0.13 mol) of 7-amino-3-chloromethyl-1-oxa-3-cephem-4-carboxylic acid diphenyl ester as a starting material and then is cooled to −20 degree C. Thereafter, 29.0 g (0.4 mol) of chlorine is injected for 60 minutes to form a first mixture. The mixture is stirred at the same temperature for 10 minutes. Then, 174.7 g (0.46 mol) of a methanol solution of 10% LiOMe (lithium methoxide) is added to the first mixture in a dropwise manner at −40 to −50 degree C. for 90 minutes to form a second mixture. Then, at the same temperature, after stirring the second mixture for 5 minutes, 6.4 g (0.11 mol) of acetic acid is added thereto. Then, 428.5 g of 10% sodium sulfite, and 400 g of purified water are added in this order to the second mixture to form a third mixture. After stirring the third mixture for 30 minutes, the methylene chloride layer is separated from the third mixture. Thereafter, the third mixture is washed using a dilute aqueous sodium bicarbonate solution. Then, 50 g of anhydrous magnesium sulfate is added to an organic layer of the third mixture, followed by stirring for 20 minutes, followed by filtration and, followed by washing with 200 g of methylene chloride. In this way, an intermediate product is obtained.

Then, 10.0 g (0.09 mol) of sodium-1-methyl-1H-tetrazole-5-thiolate and 1.5 g of tetra-n-butylammonium bromide are added to the intermediate product which in turn, is stirred at 25° C. After 1 hour, 5 g (0.04 mol) of sodium-1-methyl-1H-tetrazole-5-thiolate and 1.0 g of quaternary ammonium salt are added to the product which is further stirred for 1 hour. Thus, the reaction is terminated. In this way, a second intermediate product is obtained. Thereafter, 150 g of purified water is added the second intermediate product which in turn, is stirred at 0 degree C. for 30 minutes. An organic layer is separated from the intermediate product. The organic layer is concentrated at 80% or more, and, then, 100 g of methanol is added to the organic layer which is re-concentrated. Then, 100 g of methanol is further added to the organic layer, which in turn, is stirred at −10 DEG C. for 2 hours and then filtered. Then, the layer is washed with 50 g of methanol and vacuum-dried at 40 DEG C. for 10 hours. Eventually, a white crystalline powder, (6R, 7R)-benzhydryl-7-amino-7-methoxy-3-((1-methyl-1H-tetrazol-5-yl-thio) methyl)-8-oxo-5-oxa-1-aza-bicyclo[4.2.0]oct-2-ene-2-carboxylate (48.6 g, 72%) having following properties is obtained:

m.p.: 161 to 163° C.

H-NMR (CDCl$_3$) δ: 2.00 (2H, brs, C7-NH$_2$), 3.38 (3H, s, C7-OCH$_3$), 3.87 (3H, s, N—CH$_3$), 4.32 (2H, s, C2-CH$_2$), 4.73 (2H, s, C3-CH$_2$), 4.92 (1H. s, C6-CH), 7.00 (1H, s, CHPh$_2$), 7.25-7.59 (10H, m, C6H5, C$_6$H$_5$)

The description of the disclosed embodiments is provided to enable any person of ordinary skill in the art to make or use the present disclosure. Various modifications to these embodiments will be readily apparent to those of ordinary skill in the art of the present disclosure. Further, the generic principles defined herein may be applied to other embodiments without departing from the scope of the present disclosure. Accordingly, the present disclosure is not to be limited to the embodiments set forth herein but is to be accorded the widest scope consistent with the principles and novel features presented herein.

What is claimed is:

1. A method for preparing a 7α-alkoxyoxacephem compound, the method comprising a process (S1) including:
   (a) reacting a compound represented by a following chemical formula 1 with chlorine in an organic solvent to form a reaction product such that unreacted chlorine remains; and
   (b) adding metal alkoxide and reducing agent to the reaction product with the unreacted chlorine remaining, thereby to produce a compound represented by a following chemical formula 2:

<chemical formula 1>

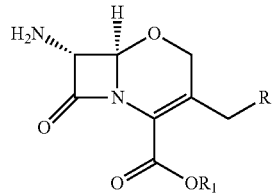

where R is a Cl, Br, or I, R$_1$ is diphenylmethyl, p-methoxybenzyl, p-nitrobenzyl, or hydrogen (H) as a carboxyl protecting group, <chemical formula 2>

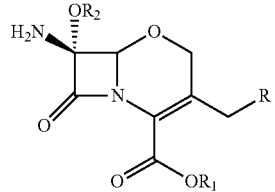

where R is a Cl, Br, or I, R$_1$ is diphenylmethyl, p-methoxybenzyl, p-nitrobenzyl or hydrogen (H) as a carboxyl protecting group, and R$_2$ is an alkyl group having 1 to 4 carbon atoms.

2. The method of claim 1, wherein a content of the organic solvent is equal to a content of the compound expressed by the chemical formula 1 or is 100 times or less larger than the content of the compound expressed by the chemical formula 1.

3. The method of claim 1, wherein a content of the chlorine is in a range of 2 to 4 mol based on a content of the compound expressed by the chemical formula 1.

4. The method of claim 1, wherein a reaction temperature in the (a) is in range of −50 to 50° C.

5. The method of claim 1, wherein the metal alkoxide includes at least one selected from a group consisting of lithium methoxide (LiOCH$_3$), lithium ethoxide, lithium tert-butoxide, sodium methoxide (NaOCH$_3$), potassium methoxide (KOCH$_3$), or magnesium methoxide (Mg(OCH$_3$)$_2$).

6. The method of claim 5, wherein a content of the metal alkoxide is in a range of 3 to 5 mol based on a content of the compound expressed as the chemical formula 1.

7. The method of claim 6, wherein a reaction temperature in the (b) is in a range of −70° C. to −20° C.

8. The method of claim 6, wherein the reducing agent includes at least one selected from a group consisting of sodium sulfite, sodium thiosulfate, sodium acid sulfite, dialkyl sulfide or phosphine.

9. The method of claim 1, wherein the method further comprises a process (S2) after the process (S1), wherein the process (S2) includes adding an acetamidating agent to the compound represented by the chemical formula 2, thereby to form a compound expresses by a following chemical formula 3:

<chemical formula 3>

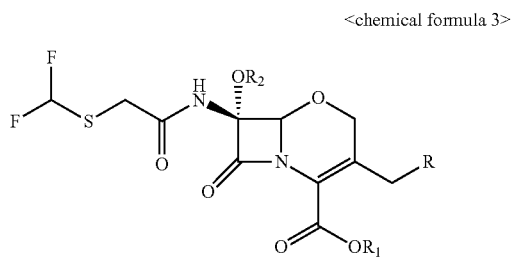

where R is a Cl, Br, or I, $R_1$ is diphenylmethyl, p-methoxybenzyl, p-nitrobenzyl, or hydrogen (H) as a carboxyl protecting group, and $R_2$ is an alkyl group having 1 to 4 carbon atoms.

10. The method of claim 9, wherein the acetamidating agent includes a compound expressed by a following chemical formula 4:

<chemical formula 4>

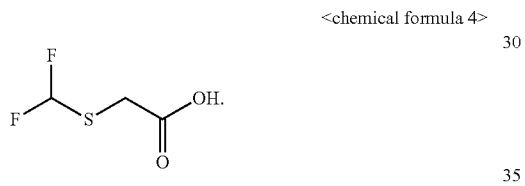

11. The method of claim 1, wherein the method further comprises a process (S3) after the process (S1), wherein the process (S3) includes adding a thiolating agent to the compound represented by the chemical formula 2, thereby to form a compound expresses by a following chemical formula 5:

<chemical formula 5>

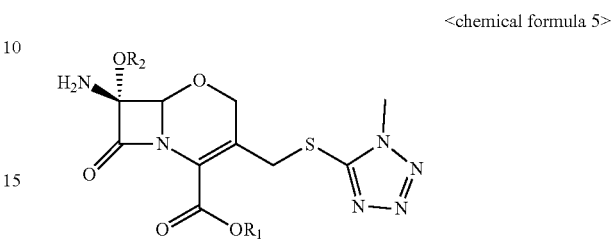

where R is a Cl, Br, or I, $R_1$ is diphenylmethyl, p-methoxybenzyl, p-nitrobenzyl, or hydrogen (H) as a carboxyl protecting group, and $R_2$ is an alkyl group having 1 to 4 carbon atoms.

12. The method of claim 11, wherein the thiolating agent includes a compound represented by a following chemical formula 6:

<chemical formula 6>

* * * * *